United States Patent [19]
Moore et al.

[11] Patent Number: 6,114,595
[45] Date of Patent: Sep. 5, 2000

[54] STRETCHABLE, EXTENSIBLE COMPOSITE TOPSHEET FOR ABSORBENT ARTICLES

[75] Inventors: Megan R. Moore, Cincinnati; Beverly J. Manring, West Chester, both of Ohio

[73] Assignee: The Procter & Gamble Company, Cincinnati, Ohio

[21] Appl. No.: 08/629,491

[22] Filed: Apr. 11, 1996

[51] Int. Cl.[7] ............................. A61F 13/15; A61F 13/20
[52] U.S. Cl. ................... 604/370; 604/378; 604/385.16; 428/116; 428/131
[58] Field of Search ................................ 604/375.2, 370, 604/379, 378, 382, 383, 381, 385.01, 385.16; 428/116, 131, 156

[56] References Cited

U.S. PATENT DOCUMENTS

| | | |
|---|---|---|
| H1377 | 11/1994 | Perry ..................................... 604/385.1 |
| 3,095,878 | 7/1963 | Bassett . |
| 3,137,746 | 6/1964 | Seymour et al. . |
| 3,260,778 | 7/1966 | Walton . |
| 3,426,405 | 2/1969 | Walton . |
| 3,597,299 | 8/1971 | Thomas et al. . |
| 3,828,784 | 8/1974 | Zoephel .................................. 604/372 |
| 3,925,127 | 12/1975 | Yoshioka . |
| 3,949,128 | 4/1976 | Ostermeier . |
| 4,090,385 | 5/1978 | Packard . |
| 4,100,017 | 7/1978 | Flautt, Jr. . |
| 4,127,637 | 11/1978 | Pietreniak et al. . |
| 4,142,278 | 3/1979 | Walton et al. . |
| 4,176,667 | 12/1979 | Herring . |
| 4,191,609 | 3/1980 | Trokhan . |
| 4,208,459 | 6/1980 | Becker et al. . |
| 4,276,339 | 6/1981 | Stoveken . |
| 4,342,314 | 8/1982 | Radel et al. ............................ 604/370 |
| 4,421,812 | 12/1983 | Plant . |
| 4,422,892 | 12/1983 | Plant . |

(List continued on next page.)

FOREIGN PATENT DOCUMENTS

| | | |
|---|---|---|
| 809627 | 4/1969 | Canada . |
| 0 307 871 B1 | 12/1992 | European Pat. Off. . |
| 1 576 716 | 10/1980 | United Kingdom . |
| 2270874 | 3/1994 | United Kingdom ................... 604/378 |
| 91/10415 | 7/1991 | WIPO . |
| 91/11161 | 8/1991 | WIPO . |
| 93/01786 | 2/1993 | WIPO . |
| WO 93/09741 | 5/1993 | WIPO . |
| 93/15701 | 8/1993 | WIPO . |
| 95/34264 | 12/1995 | WIPO . |

*Primary Examiner*—Mark O. Polutta
*Attorney, Agent, or Firm*—Roddy M. Bullock; David M. Weirich

[57] ABSTRACT

The present invention pertains, in a preferred embodiment, to a stretchable, extensible, fluid-pervious composite web comprising an apertured, three-dimensional, macroscopically-expanded formed film layer and a fibrous layer, preferably a nonwoven, bonded to one side of the formed film layer. The composite web is microcreped in at least one direction, such that the composite web exhibits extensibility, and preferably also retractability, in that direction. The composite web exhibits fine scale nesting of the formed film layer and the nonwoven layer in the microfolds, providing intimate contact between the layers for enhanced fluid transport properties while the three-dimensionality of the formed film provides a stand-off between the layers. The composite webs of the present invention are particularly suited for use as a topsheet on an absorbent article, in order to provide for enhanced stretchability and extensibility to accommodate a wide range of in-use conditions and to enable the absorbent article to better conform to the wearer's body to improve wearing comfort via enhanced flexibility. The microcreped surface also provides a soft, pleasing visual and tactile impression to the wearer. The present invention further relates to a method of making a stretchable, extensible, fluid-pervious composite web comprising the steps of: (a) providing an apertured, three-dimensional, macroscopically-expanded formed film layer; (b) providing a fibrous layer; (c) bonding the fibrous layer to one side of the formed film layer to form a composite web; (d) microcreping the composite web in at least one direction such that the composite web is contracted that direction and such that the formed film layer remains substantially three-dimensional and macroscopically-expanded.

25 Claims, 3 Drawing Sheets

U.S. PATENT DOCUMENTS

| | | |
|---|---|---|
| 4,435,458 | 3/1984 | Hill . |
| 4,463,045 | 7/1984 | Ahr et al. .................................. 604/370 |
| 4,487,796 | 12/1984 | Lloyd et al. . |
| 4,555,811 | 12/1985 | Shimalla . |
| 4,574,021 | 3/1986 | Endres et al. . |
| 4,610,743 | 9/1986 | Salmeen et al. . |
| 4,614,679 | 9/1986 | Farrington, Jr. et al. ............... 428/138 |
| 4,634,621 | 1/1987 | Manning et al. . |
| 4,704,113 | 11/1987 | Schoots ................................... 604/370 |
| 4,842,596 | 6/1989 | Kielpikowski et al. . |
| 5,066,348 | 11/1991 | Manning . |
| 5,117,540 | 6/1992 | Walton et al. . |
| 5,145,727 | 9/1992 | Potts et al. . |
| 5,149,332 | 9/1992 | Walton et al. . |
| 5,342,334 | 8/1994 | Thompson et al. ..................... 604/370 |
| 5,352,217 | 10/1994 | Curro ...................................... 604/370 |
| 5,366,782 | 11/1994 | Curro et al. . |
| 5,591,149 | 1/1997 | Cree ........................................ 604/381 |
| 5,613,962 | 3/1997 | Kenmochi et al. ..................... 604/382 |
| 5,658,639 | 8/1997 | Curro et al. ............................ 604/382 |
| 5,762,643 | 6/1998 | Ray et al. ............................... 604/383 |

STRETCHABLE, EXTENSIBLE COMPOSITE TOPSHEET FOR ABSORBENT ARTICLES

FIELD OF THE INVENTION

The present invention relates to extensible fluid pervious webs particularly suited for use as a composite topsheet in a disposable absorbent article, such as a diaper, sanitary napkin, panty liner, incontinence pad, or the like. The present invention further relates to methods for making such webs.

BACKGROUND OF THE INVENTION

All manner and variety of absorbent articles configured for the absorption of bodily fluids are, of course, well known. Current types of absorbent articles include sanitary napkins, pantiliners, disposable diapers, and incontinent articles.

One material which has been widely utilized as a topsheet material in absorbent articles is disclosed in commonly assigned U.S. Pat. No. 4,342,314 issued to Radel, et al. on Aug. 3, 1982 and hereby incorporated herein by reference. Radel, et al. discloses an absorbent bandage with a wearer-contacting topsheet comprising a resilient, macroscopically expanded, three-dimensional plastic web exhibiting a combination of fiber-like and plastic properties. In a preferred embodiment, the macroscopically expanded, three-dimensional, plastic web topsheet disclosed in Radel, et al. exhibits a fine scale three-dimensional microstructure comprising a regulated continuum of capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel, et al. structure comprises an uppermost capillary opening or aperture formed by a multiplicity of fiber-like elements interconnected to one another in the uppermost plane of the web. Each of the fiber-like elements exhibits a substantially uniform U-shaped cross-section along its length. The cross-section of the fiber-like element comprises a base portion located in the wearer-contacting plane and a sidewall portion joined to each edge of the base portion, the sidewall portions extend generally in the direction of the absorbent pad-contacting surface of the web. The sidewall portions which intersect one another are joined to one another intermediate the wearing contacting surface and the absorbent pad contacting surface of the web, thereby forming a capillary network interconnecting the opposed surfaces of the web.

A topsheet of the type generally disclosed by Radel, et al. is highly effective in promoting rapid fluid transfer from the first, wearer-contacting surface to the second, absorbent pad-contacting surface of the topsheet. Accordingly, topsheets of this type have enjoyed widespread commercial success on catamenial pads due to their clean and dry appearance in use when contrasted to conventional non-woven fibrous topsheets or two-dimensional films. While an absorbent article having a topsheet of the type disclosed in Radel, et al. is highly effective in promoting rapid transfer of bodily fluids from the first, wearer-contacting surface to the second, absorbent pad-contacting surface, the degree of masking of bodily fluids, e.g., menses, retained within the absorbent core is dependent upon the size of the capillary networks. As the size of the capillary networks decrease the amount of masking provided by the topsheet increases. However, if the capillary networks are too small bodily fluids are not able to pass through the topsheet into the absorbent core thereby exposing the skin to moisture. Furthermore, the three-dimensional structure of the film tends to limit its ability to expand and contract in sheet-wise dimension (extensibility) in response to in-use forces, in turn limiting the ability of the absorbent article to accommodate various postures and activities of the wearer. Due to their three-dimensional structure and the molecular orientation imparted to the formed film during the formation process, it has been difficult to impart extensibility and additional softness to such films via post-formation mechanical processes without causing destruction and/or damage to the three-dimensional capillary structure and hence degradation in fluid handling performance.

Conventional nonwoven topsheets have been found to provide desirable visual and tactile properties from the wearer's perspective, as well as good flexibility and softness properties. However, the fluid-handling performance of conventional nonwoven topsheets has been found to be less than optimal, particularly with comparatively more viscous bodily fluids, contributing to a "wet" tactile impression after exposure to bodily fluids. In addition, while conventional nonwoven topsheets provide a masking effect with regard to the underlying absorbent article components, residual fluid remaining within the nonwoven material itself after use creates a less-than-desirable visual impression. Unlike formed film materials, nonwovens utilized for topsheet applications have been comparatively easier to subject to post-formation mechanical processes to impart extensibility and additional softness while maintaining their original properties.

Accordingly, it would be desirable to provide a fluid pervious web suitable for use as a topsheet in an absorbent article which provides the fluid handling capabilities of a formed film material and the softness of a nonwoven material.

It would also be desirable to provide a topsheet material having desirable visual and tactile properties, including a soft tactile impression.

It would be further desirable to provide such a topsheet material which provides sufficient stretchability and extensibility to accommodate a wide range of in-use conditions and to enable the absorbent article to better conform to the wearer's body.

SUMMARY OF THE INVENTION

The present invention pertains, in a preferred embodiment, to a stretchable, extensible, fluid-pervious composite web comprising an apertured, three-dimensional, macroscopically-expanded formed film layer and a fibrous layer bonded to one side of the formed film layer. The composite web is microcreped in at least one direction, such that the composite web exhibits extensibility, and preferably also retractability, in that direction.

The composite web exhibits fine scale nesting of the formed film layer and the fibrous layer in the microfolds, providing intimate contact between the layers for enhanced fluid transport properties while the three-dimensionality of the formed film provides a stand-off between the layers. Accordingly, composite webs of the present invention provide the fluid handling properties of a formed film and the softness properties of a nonwoven material, as well as the desired extensibility.

The composite webs of the present invention are particularly suited for use as a topsheet on an absorbent article, in order to provide for enhanced stretchability and extensibility to accommodate a wide range of in-use conditions and to enable the absorbent article to better conform to the wearer's body to improve wearing comfort via enhanced flexibility. The microcreped surface also provides a soft, pleasing visual and tactile impression to the wearer.

The present invention further relates to a method of making a stretchable, extensible, fluid-pervious composite web comprising the steps of: (a) providing an apertured, three-dimensional, macroscopically-expanded formed film layer; (b) providing a fibrous layer; (c) bonding the fibrous layer to one side of the formed film layer to form a composite web; (d) microcreping the composite web in at least one direction such that the composite web is contracted that direction and such that the formed film layer remains substantially three-dimensional and macroscopically-expanded. Accordingly, the process of the present invention substantially preserves the three-dimensional structure of the formed film and thus maintains its fluid transport properties.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
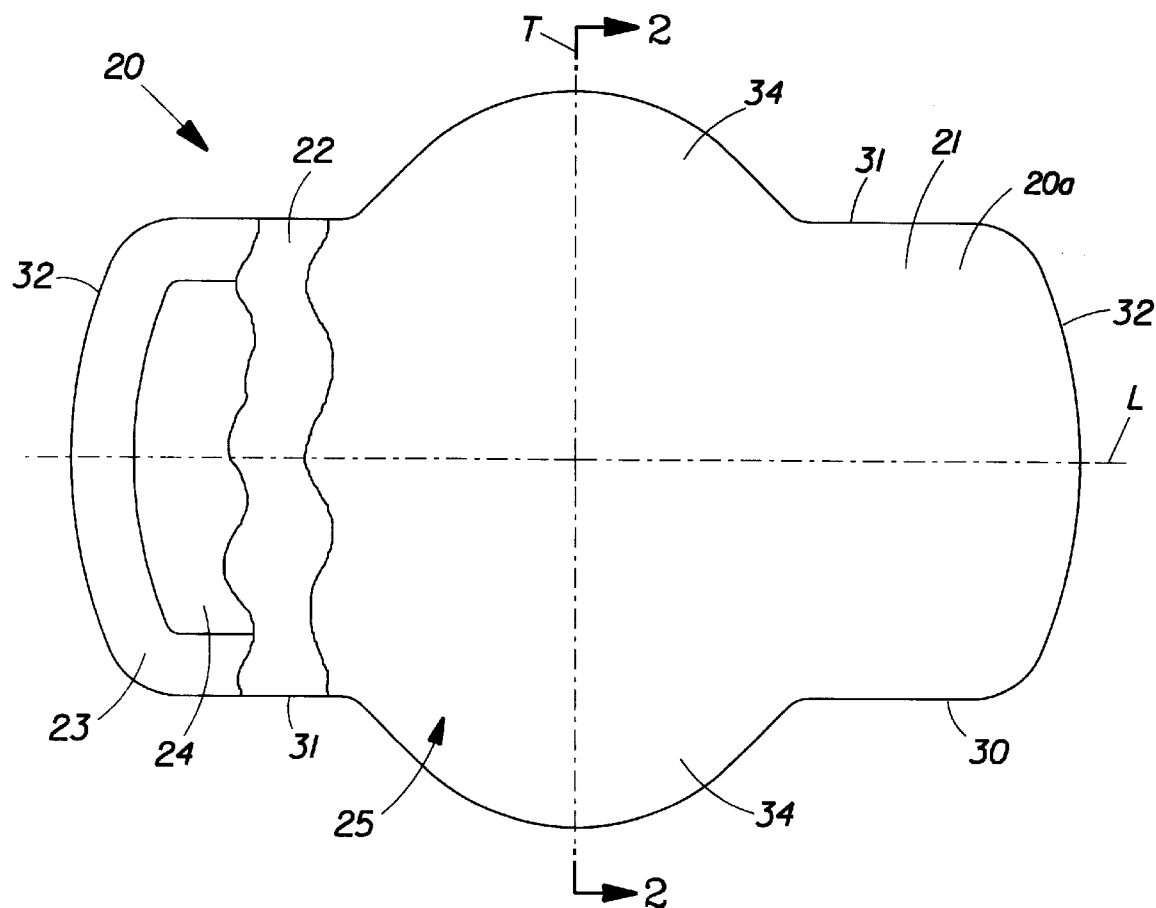
FIG. 1 is a top plan view of an absorbent article in the form of a sanitary napkin with portions cut-away to more clearly show the construction of the sanitary napkin.

A presently preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, incontinence briefs, and the like.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a composite topsheet 25 having a first or body facing fluid pervious topsheet layer 21 and a second or garment facing fluid pervious topsheet layer 22, a fluid impervious backsheet 23 joined with composite topsheet 25, and an absorbent core 24 positioned between the composite topsheet 25 and the backsheet 23.

The sanitary napkin 20 has two surfaces, a body-contacting surface or body facing surface 20a and a garment facing surface 20b. The sanitary napkin 20 is shown in FIG. 1 as viewed from its body facing surface 20a. The body facing surface 20a is intended to be worn adjacent to the body of the wearer while the garment facing surface 20b is on the opposite side and is intended to be placed adjacent to the wearer's undergarments or clothing when the sanitary napkin 20 is worn. The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

FIG. 1 shows a preferred embodiment of the sanitary napkin 20 in which the composite topsheet 25 and the backsheet 23 have length and width dimensions generally larger than those of the absorbent core 24. The composite topsheet 25 and the backsheet 23 extend beyond the edges of the absorbent core 24 to thereby form not only portions of the periphery but also side flaps 34.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
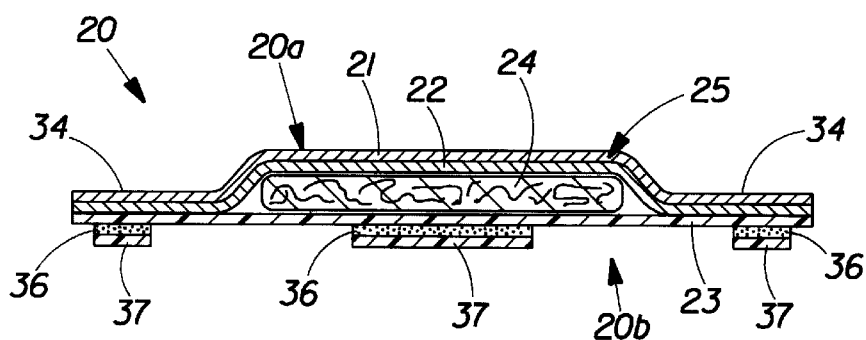
FIG. 2 is a cross-sectional view of the sanitary napkin of FIG. 1 taken along the section line 2—2.

FIG. 2 is a cross-sectional view of the sanitary napkin 20 taken along transverse section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than a crotch portion of the undergarment prior to use or experiencing contamination and degradation.

The sanitary napkin 20 can be of any thickness, including relatively thick or relatively thin. The embodiment of the sanitary napkin 20 shown in FIGS. 1 and 2 is intended to be an example of a relatively thin sanitary napkin. It should be understood, however, when viewing these figures that the number of layers of material shown tends to cause the sanitary napkin to appear much thicker than it actually is. A "thin" sanitary napkin 20 preferably has a caliper of less than about 3 millimeters. The thin sanitary napkin 20 shown should also be relatively flexible, so that it is comfortable for the wearer.

Preferably, the sanitary napkin is extensible or stretchable. Examples of extensible or stretchable sanitary napkins are disclosed in commonly-assigned, co-pending U.S. patent applications Ser. No. 07/915,133, filed Jul. 23, 1992 in the names of Osborn, et al., and Ser. No. 07/913,204, filed Jul. 23, 1992 in the names of Osborn, et al., the disclosures of which are hereby incorporated herein by reference.

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation EL-2238. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

In a preferred embodiment of the present invention, the sanitary napkin 20 has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps 34 serve at least two purposes. First, the flaps 34 help serve to prevent soiling of the wearer's body and panties by menstrual fluid, preferably by forming a double wall barrier along the edges of the panty. Second, the flaps 34 are preferably provided with attachment means on their garment surface so that the flaps can be folded back under the panty and attached to the garment facing side of the panty. In this way, the flaps 34 serve to keep the sanitary napkin 20 properly positioned in the panty. The flaps 34 can be constructed of various materials including materials similar to the topsheet, backsheet, tissue, or combination of these materials. Further, the flaps 34 may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat. No. 4,608,047 issued to Mattingly on Aug. 26, 1986. Each of these patents are incorporated herein by reference.

The absorbent core 24 may be any absorbent means which is capable of absorbing or retaining liquids (e.g., menses and/or urine). As shown in FIG. 1, the absorbent core 24 has a body facing surface, a garment facing surface, side edges, and end edges. The absorbent core 24 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core 24 may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core may be varied to accommodate different uses such as incontinence pads, pantiliners, regular sanitary napkins, or overnight sanitary napkins. In addition, the absorbent core 24 may be comprised of certain materials or configurations to provide flexibility, if so desired.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 23 and the composite topsheet 25 are positioned adjacent the garment facing surface and the body facing surface, respectively, of the absorbent core 24 and are preferably joined thereto and to each other by attachment means (not shown) such as those well known in the art. For example, the backsheet 23 and/or the composite topsheet 25 may be secured to the absorbent core 24 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., under the designation HL-1258, and by Findley of Minneapolis, Minn., under the designation H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 has a body facing surface and a garment facing surface. The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

The composite topsheet 25 according to the present invention is compliant, soft feeling, and non-irritating to the wearer's skin. Further, the composite topsheet 25 is liquid pervious permitting liquids (e.g., menses and/or urine) to readily penetrate through its thickness. Composite topsheet 25 includes an apertured formed film of a polymeric film material, such as polyethylene, polypropylene, or other suitable material, as a first body facing topsheet layer 21. Apertured formed films are preferred because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; U.S. Pat. No. 4,637,819 issued to Ouellette, et al. on Jan. 20, 1987, and U.S. Pat. No. 5,006,394 issued to Baird on Apr. 9, 1991. Each of these patents are incorporated herein by reference. Other suitable formed films include hydroformed films such as those disclosed in U.S. Pat. No. 4,629,643, issued Dec. 16, 1986 to Curro et al., and U.S. Pat. No. 4,609,518, issued Sep. 2, 1986 to Curro, both of which are also hereby incorporated herein by reference. Preferred forms of hydroformed films would include those having microapertures formed therein.

Figure 3:
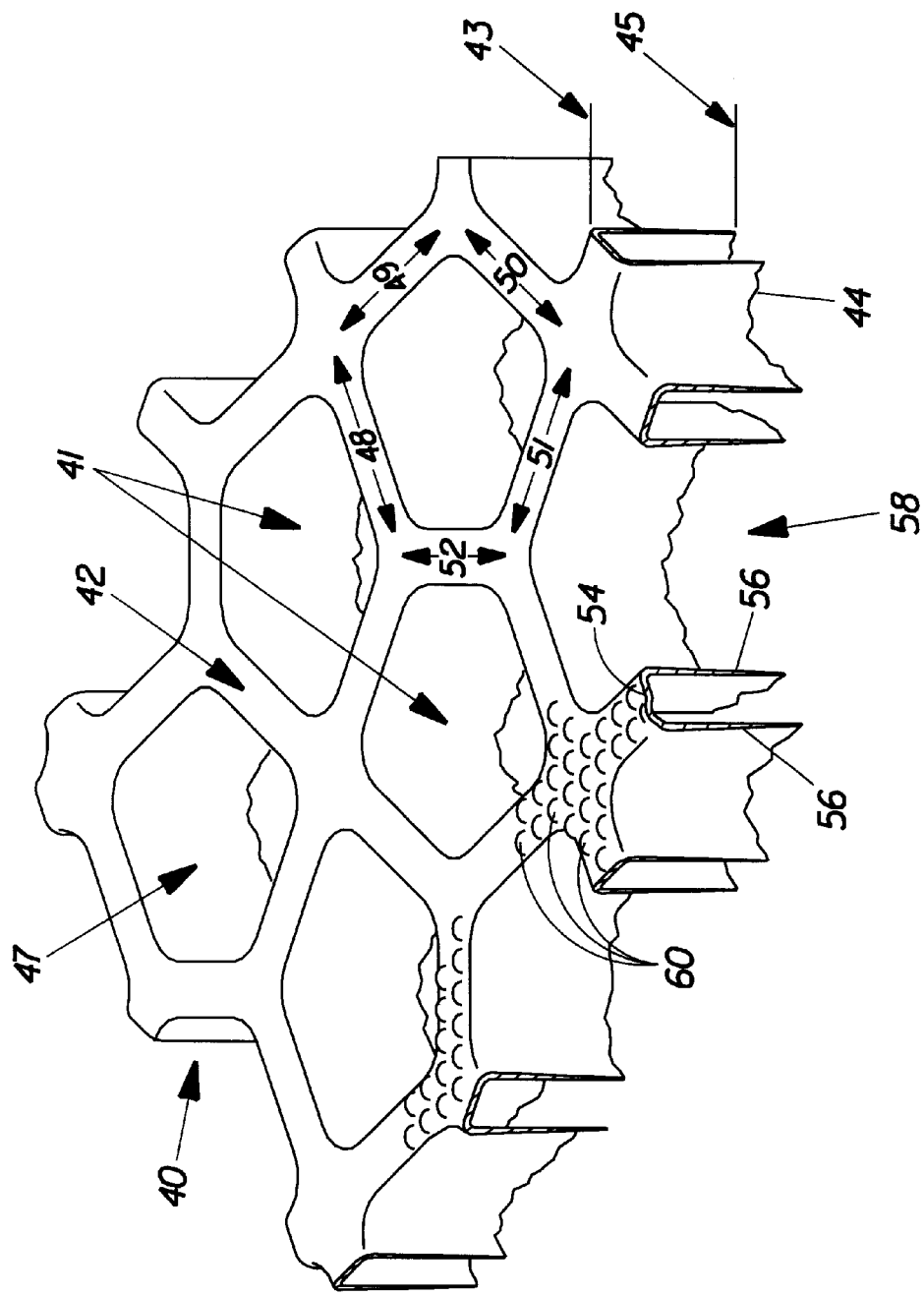
FIG. 3 is an enlarged, partially segmented, perspective illustration of a preferred fluid pervious web suitable for use as the first layer of the composite web of the present invention.

FIG. 3 is an enlarged, partially segmented, perspective illustration of a particularly preferred embodiment of an apertured, macroscopically expanded, three-dimensional, fiber-like, fluid pervious, polymeric web 40, generally in accordance with the teachings of commonly assigned U.S. Pat. No. 4,342,314 issued to Radel et al. on Aug. 3, 1982, which has been found suitable for use as the first topsheet layer 21 of composite topsheet 25 on sanitary napkin 20. The term "macroscopically expanded", when used to describe three-dimensional plastic webs of the present invention, refers to webs, ribbons and films which have been caused to conform to the surface of a three-dimensional forming structure so that both surfaces thereof exhibit a three-dimensional forming pattern of surface aberrations corresponding to the macroscopic cross-section of the forming structure, the surface aberrations comprising the pattern are individually discernible to the normal naked eye, i.e., a normal naked eye having 20/20 vision unaided by an instrument that changes the apparent size or distance of an object or otherwise alters the visual powers of the eye, when the perpendicular distance between the viewer's eye and the plane of the web is about 12 inches. The term "fiber-like", as utilized herein to describe the appearance of plastic webs of the present invention, refers generally to any fine scale pattern of apertures, random or non random, reticulated or non-reticulated, which connote an overall appearance and impression of a woven or nonwoven fibrous web when viewed by the human eye.

As can be seen in FIG. 3, the web's fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 41. The web 40 which exhibits a fiber-like appearance, embodies a three-dimensional microstructure extending from the webs uppermost, wearer-contacting or body facing surface 42 in plane 43 to its lowermost or garment facing surface 44 in plane 45 to promote rapid fluid transport from the uppermost surface 42 to the lowermost surface 44 of the web without lateral transmission of fluid between adjacent capillaries 41. As utilized herein, the term "microstructure" refers to a structure of such fine scale that its precise detail is readily perceived by the human eye only upon magnification by microscopic or other means well known in the art.

Apertures 47 in the body surface 42 are formed by a multiplicity of intersecting fiber-like elements, e.g., elements 48, 49, 50, 51, and 52, interconnected to one another in the body facing surface of the web. Each fiber-like element comprises a base portion, e.g., base portion 54, located in plane 43. Each base portion has a sidewall portion, e.g., sidewall portions 56, attached to each edge thereof. The sidewall portions 56 extend generally in the direction of the second surface 44 of the web. The intersecting sidewall portions of the fiber-like elements are interconnected to one another intermediate the first and second surfaces of the web and terminate substantially concurrently with one another in the plane 45 of the second surface.

In the particularly preferred embodiment shown in FIG. 3, the interconnected sidewall portions 56 terminate substantially concurrently with one another in the plane of the second surface 45 to form apertures 58 in the second surface 45 of the web. The network of capillaries 41 formed by the interconnected sidewall portions 56 between apertures 47 and 58 allows for free transfer of fluids from the body facing surface of the web directly to the garment facing surface of the web without lateral transmission of the fluid between adjacent capillaries.

The base portion 54 preferably includes a microscopic pattern of surface aberrations 60, generally in accordance with the teachings of commonly assigned U.S. Pat. No. 4,463,045 issued to Ahr et al. on Jul. 31, 1984. The microscopic pattern of surface aberrations 60 provide a substantially non-glossy visible surface when the web 40 is struck by incident light rays.

The first topsheet layer 21 may optionally be comprised of a multilayer polymeric film which exhibits an opaque appearance. Such a multilayer film includes a first outer layer comprised substantially of a polymeric material and a central filler-containing polymeric layer substantially continuously joined to one side of the first outer layer. The central filler-containing layer may include about 20 to 60 weight percent fillers relative to the filler-containing layer which are substantially uniformly dispersed therein. A filler such as titanium dioxide or carbonate may be used to give the topsheet a whitish, opaque appearance. The central filler-containing layer has a thickness from about 30 to about 70 percent of the total thickness of the multilayer film. A second outer layer comprised substantially of a polymeric material has one side substantially continuously joined to the second side of the central filler-containing layer. The total multilayer film preferably has at least 20 weight percent filler relative to the total multilayer film. A suitable example of such a multilayer topsheet is found in commonly assigned U.S. Pat. No. 5,261,899, issued Nov. 16, 1993 to Visscher and Perry, which is hereby incorporated herein by reference.

Preferred polymeric materials for the outer layers and the central filler-containing layer include polyolefins, particularly polyethylenes, polypropylenes and copolymers having at least one olefinic constituent. Other materials such as polyesters, nylons, copolymers thereof and combinations of any of the foregoing may also be suitable.

The second topsheet layer 22 comprises a fluid-pervious fibrous web preferably comprising a woven or nonwoven web formed of synthetic fibers (such as polypropylene, polyester, or polyethylene), natural fibers (such as wood, cotton, or rayon), or combinations of natural and synthetic fibers, as well as various paper, tissue, or paper-like fibrous materials. Nonwoven webs may be apertured by techniques known in the art such as needle punching, hydroentangling, ring-rolling, etc. Suitable nonwoven materials can be formed by various processes such as carding, spun-bonding, hydro-entangling, and other processes familiar to those knowledgeable in the art of nonwovens. The fibers of the nonwoven material itself may be bonded to one another to provide integrity to the material by any of a number of suitable methods, including heat bonds, pressure bonds, ultrasonic bonds, dynamic mechanical bonds, or any other means known in the art.

Fibrous materials suitable for use in the present invention may either exhibit inherent porosity due to interfiber spacing and/or porosity due to formed apertures extending through the material. Porosity may be provided or enhanced by various mechanical means such as punching, slitting, severing, ring-rolling, hydro-entangling, or any other suitable method.

A presently preferred fibrous material comprises a spun-bond polypropylene nonwoven commercially available from Fiberweb of Simpsonville, S.C., under the trade designation P9. Another fibrous material which has been found suitable is a synthetic carded nonwoven commercially available from Havix of Japan under the trade designation Havix S2146. Fibrous webs suitable for use in the composite webs of the present invention may be inherently extensible or non-extensible in their original form, prior to the microcreping operation described below.

The first and second topsheet layers are bonded to one another to form the composite topsheet 25 by any one of the various bonding methods known in the art. Suitable methods include adhesive bonding such as a uniform continuous layer of adhesive, a patterned layer of adhesive, or an array of separate lines, spirals, or spots of adhesive, or other methods such as heat bonds, pressure bonds, ultrasonic bonds, dynamic mechanical bonds, or any other suitable attachment means or combinations of these attachment means as are known in the art. Representative bonding methods are also described in the above-referenced published PCT application WO 93/09741, entitled "Absorbent Article Having A Nonwoven and Apertured Film Coversheet", published May 27, 1993 naming Aziz et al. as inventors, incorporated herein by reference. A presently preferred bonding method comprises dynamic mechanical bonding, also known as point thermal bonding. Such a bonding method provides a suitable bond between the layers of the composite topsheet which has sufficient integrity to survive the microcreping process yet does not occlude the apertures in the formed film layer. Particularly when this bonding method is utilized, it is preferred that the materials utilized for the formed film layer and the fibrous layer (first and second topsheet layers, respectively) be thermally similar (i.e., have a similar melting temperature and melting properties).

In accordance with the present invention, it is preferred that at least the body facing surfaces of the topsheet layers are hydrophilic so as to help liquid to transfer through the topsheets faster than if the body facing surface was not hydrophilic so as to diminish the likelihood that menstrual fluid will flow off the topsheets rather than flowing into and being absorbed by the absorbent core. Alternatively, on or both topsheet layers could be hydrophobic, at least to a degree. In a preferred embodiment, the topsheet layers are made hydrophilic by treating them with a surfactant such as is described in the above referenced U.S. Pat. No 4,950,254 issued to Osborn, incorporated herein by reference. Alternatively, surfactant may be incorporated into the polymeric materials of the topsheet layers (where applicable) such as is described in the above-referenced published PCT application WO 93/09741, entitled "Absorbent Article Having A Nonwoven and Apertured Film Coversheet", published May 27, 1993 naming Aziz et al. as inventors, incorporated herein by reference. In a preferred embodiment, the first topsheet layer is less hydrophilic than the second topsheet layer.

Figure 4:
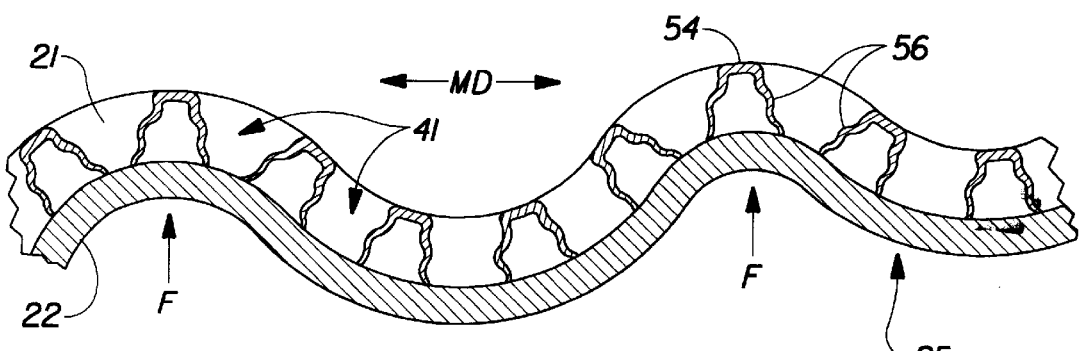
FIG. 4 is an enlarged, cross-sectional view of the composite web according to the present invention depicted in FIGS. 1 and 2.

FIG. 4 depicts the composite topsheet 25 in much greater detail, such as would be visible when viewed through a microscope or other visual magnification aid, and in particular the relationship between the first topsheet layer 21 and the second topsheet layer 22 after they have been bonded to one another and microcreped. More particularly, FIG. 4 depicts the fine scale nesting of the two layers throughout the small folds imparted by the microcreping process. As shown in FIG. 4, the first topsheet layer 21 substantially retains its three-dimensionality and macroscopic expansion (i.e., the capillary structure of the formed film material is not substantially compressed, flattened, or deformed), with the degree to which the three-dimensionality and macroscopic expansion is maintained dependent upon the processing conditions during the microcreping procedure and upon the characteristics of the particular fibrous layer employed.

The fibrous layer, particularly when oriented such that it is bonded to the side of the formed film where the capillaries open, tends to cushion and protect the formed film structure during the microcreping process such that the capillaries experience less direct force application and hence less collapse. The benefit of this characteristic is that the three-dimensional formed film maintains its inherent fluid handling properties particularly desirable for topsheet applications on absorbent articles. The natural resiliency of the three-dimensional, macroscopically-expanded capillary structure provides a "stand-off" or spacing between the formed film and fibrous layer, and hence a built-in void volume between the layers which provides for enhanced fluid acquisition properties. As such, the first topsheet layer 21 even though microcreped substantially retains the fluid handling properties of the starting formed film material.

In viewing FIG. 4, the machine direction (MD) represents the direction along which the composite topsheet or web was fed into the microcreping apparatus for microcreping. Accordingly, a number of small folds or microfolds (F) are imparted to the material which extend in a direction generally perpendicular to the machine direction MD. Due to the nature of the microcreping process and the materials utilized, these microfolds are at least to some extent durably imparted to the composite topsheet material. During the exertion of an externally-applied force in the machine direction MD, these microfolds respond by yielding under load and moving toward the centerline of the web, thereby extending the web in the machine direction in an effort to relieve the stress caused by the externally-applied force. The cross-machine direction microfolds therefore impart machine direction extensibility to the composite topsheet. In addition, in a preferred configuration the materials selected for use in the composite web are such that the microcreped composite web also exhibits retractability, or a tendency to return to the microcreped orientation when an externally-applied force is released. In this fashion, the extensibility is preferably a repeatable property in response to the full range of in-use conditions, rather than a one-time extension or permanent elongation.

In a preferred configuration, the topsheet layers are co-extensive and both fully extend to the outermost edges of the absorbent article. However, in other variations of the preferred configuration, the first and second topsheet layers need not be coextensive (i.e., they need not have the same overall size and/or shape). More particularly, while the first topsheet layer and the backsheet will typically generally define the overall size and shape of the absorbent article, the second topsheet layer may be smaller in lateral extent than the first topsheet layer in one or more directions. The second topsheet layer may therefore be sufficiently smaller than the first topsheet layer so as to be free of the peripheral bond joining the first topsheet layer and the backsheet.

Figure 5:
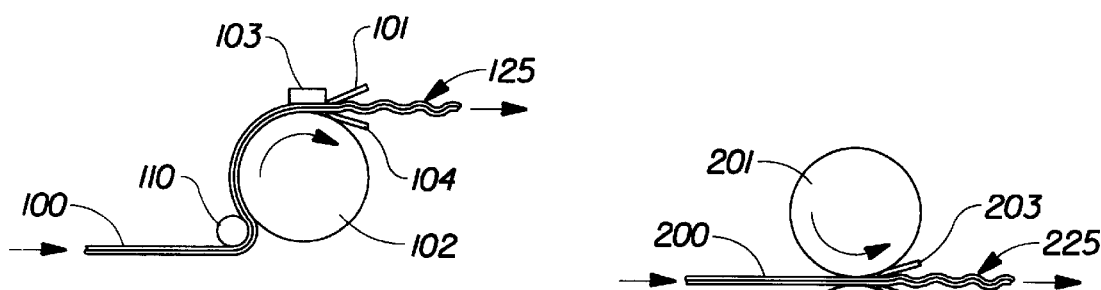
FIG. 5 is a simplified schematical illustration of a process and apparatus for forming a composite web according to the present invention.
Figure 6:
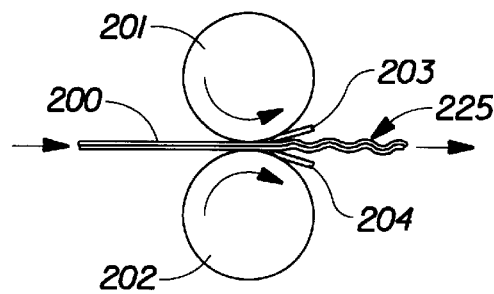
FIG. 6 is a simplified schematical illustration of another process and apparatus for forming a composite web according to the present invention.

FIGS. 5 and 6 depict in simplified schematical form two alternative microcreping processes and apparatuses which have proven suitable for forming composite topsheet webs in accordance with the present invention. In accordance with the processes of both FIGS. 5 and 6, the layers of the composite web have already been associated with one another and bonded together (sufficiently so as to survive the microcreping process intact) such that the microcreping of both layers of the composite web is performed simultaneously rather than microcreping the layers individually and bonding them together afterward.

FIG. 5 is a greatly simplified schematical illustration of a microcreping process in which a doctor blade 101 retards the uppermost surface of the composite web 100 as it is drawn between a cylindrical roll 102 and a retarder shoe 103, thereby causing the composite web to be compacted in the machine direction. A guide roll 110 or similar device guides the incoming uncreped composite web 100 into contact with the roll 102, while a second doctor blade 104 aids in the removal of the microcreped composite web 125 from the roll. The type of process and apparatus depicted in FIG. 5 is described in greater detail in a number of publications, including U.S. Pat. Nos. 3,260,778, issued Jul. 12, 1966 to Walton, and 3,426,405, issued Feb. 11, 1969 to Walton, the disclosures of which are hereby incorporated herein by reference.

FIG. 6 is a greatly simplified schematical illustration of an alternative and presently preferred microcreping process in which an upper cylindrical roll 201 and a lower cylindrical roll 202 form a nip to contact the composite web 200 at their closest point. Doctor blades 203 and 204 exert a retarding force on the surface of the composite web as it is drawn through the nip and aid in the removal of the microcreped composite web 225 from the surfaces of the rolls. The type of process and apparatus depicted in FIG. 6 is described in greater detail in a number of publications, including U.S. Pat. Nos. 4,142,278, issued Mar. 6, 1979 to Walton et al., and 5,117,540, issued Jun. 2, 1992 to Walton et al., the disclosures of which are hereby incorporated herein by reference.

Regardless of whether the microcreping utilized is accomplished via the apparatus of FIG. 5 or the apparatus of FIG. 6, or any suitably equivalent apparatus for performing the microcreping function, the resulting web configuration is substantially similar and generally as depicted in FIG. 4. The microcreping process results in the compaction of the composite web in the machine direction, compressing the material itself and imparting sequential small cross-machine-direction micro-folds to the composite web. When the microcreped composite web is thereafter subjected to a force in the former machine direction, the composite web exhibits extensibility via the ability of the small micro-folds to unfold in response to the externally-applied force. If desired, the composite web may be sequentially or simultaneously microcreped in more than one direction so as to thus exhibit extensibility in more than one direction.

Unlike some materials frequently utilized as topsheet materials for absorbent articles, and materials more commonly subjected to microcreping processes, three-dimensional, macroscopically expanded, formed film webs such as those of the present invention exhibit a strong tendency to return toward their initial as-formed configuration. More particularly, the formed film tends to return toward its pre-microcreped orientation. To overcome this tendency, in accordance with the present invention the material of the composite web, including the formed film layer, is subjected to an elevated temperature during the microcreping procedure and thereafter allowed to cool to an ambient temperature. The elevated temperature is preferably above the glass transition temperature of the polymeric film material (and preferably above that of any other synthetic components of the composite web) such that the molecular structure may be re-oriented during the microcreping process so that the composite web remains in the microcreped orientation, which is "locked in" thereafter by returning the composite web to ambient temperature before it can return to pre-creped configuration. Elevated temperatures which have proven suitable for the materials described above, in a preferred configuration, have been in the range of between about 95° F. and about 120° F. Depending upon the particular materials utilized, the microcreping temperature may be tailored to obtain the desired microcreped configuration and to maintain that orientation. Heat may be applied to the composite web to elevate its temperature by any suitable method known in the art such as, by way of example, heated rolls and heated air streams, and likewise cooling of the microcreped composite web may be accomplished by conventional methods such as chilled rolls, cool air streams, and the like. After the microcreping process is complete, the composite web may be further processed or stored for later use.

In a variation of the process of the present invention, the structure and surface characteristics of the formed film may be more suitably preserved by protecting the wearer-contacting surface of the formed film from contact with the rolls, retarders, and/or doctor blades of the microcreping apparatus. The protecting of the formed film layers of the composite webs may be accomplished by associating and superimposing two similar separate composite webs with their formed film sides facing one another, or longitudinally folding a single composite web upon itself, or superimposing a separate fibrous web upon the formed film layer of a composite web, or any other suitable method. The formed film layer of the composite web is thus protected from exposure direct shearing forces, abrasion, and heat during processing in view of the comparatively more durable fibrous material. After the microcreping of the protected composite web is accomplished, the protective separate fibrous web (or additional composite web) may be removed and the composite web may be farther processed or stored for later use.

Figure 7:
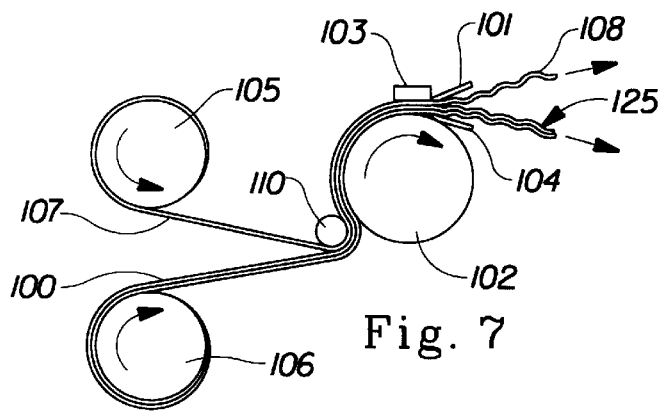
FIG. 7 is a simplified schematical illustration of a process and apparatus similar to that of FIG. 5, but including a separate fibrous web to protect the formed film layer.

FIG. 7 depicts one such variation of the process of the present invention, depicting the feeding of a separate sheet of fibrous material 107 from a feed roll 105 onto the formed film layer of a composite web 100 (fed from supply roll 106) and into the microcreping apparatus depicted in FIG. 5, the microcreped separate sheet 108 being separated from the microcreped composite web 125 after the microcreping procedure has been completed.

Figure 8:
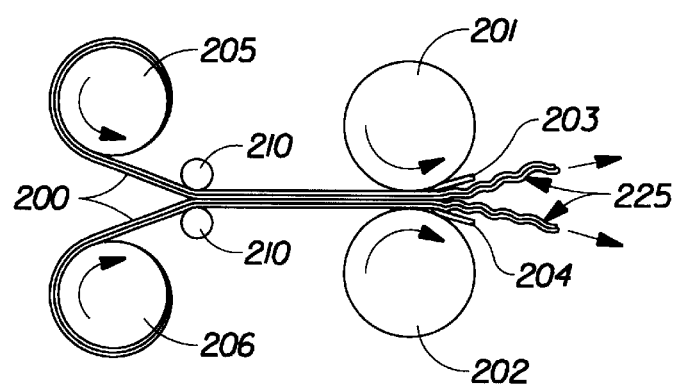
FIG. 8 is a simplified schematical illustration of a process and apparatus similar to that of FIG. 6, but including two composite webs with the formed film layers facing one another.

FIG. 8 depicts another variation of the process of the present invention, depicting the feeding of two composite webs 200 from two feed rolls 205 and 206 through guide rolls 210 and into the microcreping apparatus depicted in FIG. 6 with the formed film sides of the respective composite webs facing one another and the fibrous layers facing outwardly toward the microcreping apparatus. In this fashion the apparatus contacts and acts upon the fibrous layers of the respective composite webs to perform the microcreping function, after which the microcreped composite webs 225 may be separated for further independent processing.

Although FIG. 7 depicts the use of a separate fibrous web with the single roll microcreping apparatus of FIG. 5 and FIG. 8 depicts the use of two composite webs with the two-roll microcreping apparatus of FIG. 6, it should be recognized that either method of protecting the formed film layer of a composite web may be employed with either type of microcreping apparatus. In addition, other means of protecting formed film layers during processing may be employed, such as a recirculating padded belt or other suitable method.

Various parameters and conditions of the microcreping process may be tailored to provide the desired microcreping characteristics for a particular composite web configuration in a manner known to those skilled in the art and as described, for example, in the aforementioned Walton/Walton et al. patents already incorporated herein by reference. By way of example, the pressure imparted to the composite web by the rolls and the doctor blades may be adjusted as desired, with greater pressures in general providing a higher degree of microcreping. The angle of the doctor blades relative to the roll/composite web/doctor blade interface may also be adjusted as desired, and various types/designs of doctor blades may be utilized, with blades having non-stick surfaces being presently preferred. The tension of the composite web during the microcreping operation may also be adjusted as desired, with greater levels of tension generally tending to produce lower levels of microcreping, and accordingly lower levels of extensibility. In addition, various additives may be incorporated into the materials of the formed film layer and/or the fibrous layer or applied to their surfaces before or during the microcreping process to enhance their lubricity and/or processability, such as, for example, silicone coatings, surfactants, etc.

Not only is the degree of extensibility imparted to the composite web important, but the responsiveness of the web to external forces is also important in determining its suitability for particular applications. More particularly, it has been found to be particularly desirable in selecting composite topsheet materials for use in absorbent articles to select materials having a comparatively low force to extend, i.e., a low elastic modulus. Such materials are therefore responsive to external forces without adding additional resiliency and/or rigidity to the absorbent article that in turn negatively impacts upon comfort for the wearer.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stretchable, extensible, fluid-pervious composite web, said web comprising:

(a) an apertured, three-dimensional, macroscopically-expanded formed film layer; and (b) a fibrous nonwoven layer bonded to one side of said formed film layer; wherein said composite web is microcreped in at least one direction, such that said composite web exhibits extensibility in said direction and said formed film layer remains substantially three-dimensional and macroscopically-expanded.

2. The composite web of claim 1, wherein said composite web also exhibits retractability in said direction.

3. The composite web of claim 1, wherein said fibrous layer comprises a nonwoven material.

4. The composite web of claim 3, wherein said fibrous layer comprises an apertured nonwoven material.

5. The composite web of claim 3, wherein said fibrous layer comprises a non-apertured nonwoven material.

6. The composite web of claim 1, wherein said fibrous layer comprises a woven material.

7. The composite web of claim 6, wherein said fibrous layer comprises an apertured woven material.

8. The composite web of claim 6, wherein said fibrous layer comprises a non-apertured woven material.

9. The composite web of claim 1, wherein said formed film layer and said fibrous layer are mechanically bonded.

10. The composite web of claim 1, wherein said formed film layer and said fibrous layer are adhesively bonded.

11. The composite web of claim 1, wherein said formed film layer and said fibrous layer are thermally bonded.

12. The composite web of claim 1, wherein said composite web exhibits fine scale nesting of said formed film layer and said fibrous layer.

13. The composite web of claim 1, wherein said composite web is microcreped in more than one direction, such that said composite web exhibits extensibility in more than one direction.

14. The composite web of claim 1, wherein said fibrous layer comprises a natural nonwoven material.

15. The composite web of claim 1, wherein said fibrous layer comprises a synthetic nonwoven material.

16. The composite web of claim 1, wherein said fibrous layer comprises a blended nonwoven material of natural and synthetic fibers.

17. The composite web of claim 1, wherein said formed film layer and said fibrous layer are thermally similar.

18. An absorbent article comprising:
  (a) a stretchable, extensible, fluid-pervious composite web having a body facing side and a garment facing side, said web including:
    (i) an apertured, three-dimensional, macroscopically-expanded formed film layer; and
    (ii) a fibrous nonwoven layer bonded to one side of said formed film layer;
    said composite web being microcreped in at least one direction, such that said composite web exhibits extensibility in said direction and said formed film layer remains substantially three-dimensional and macroscopically-expanded;
  (b) an absorbent core underlying said composite topsheet, said absorbent core having a body facing surface and a garment facing surface; and
  (c) a backsheet underlying said absorbent core, said backsheet having a body facing surface and a garment facing surface.

19. The absorbent article of claim 18, wherein said composite web also exhibits retractability in said direction.

20. The absorbent article of claim 18, wherein said formed film layer comprises said body facing side of said composite web and said fibrous layer comprises said garment facing side of said web.

21. The absorbent article of claim 18, wherein said fibrous layer comprises said body facing side of said composite web and said formed film layer comprises said garment facing side of said web.

22. The absorbent article of claim 18, wherein said absorbent article has a longitudinal centerline and a transverse centerline, and wherein said direction is parallel to said longitudinal centerline.

23. The absorbent article of claim 18, wherein said absorbent article is stretchable in said direction.

24. The absorbent article of claim 18, wherein said fibrous layer comprises a nonwoven material.

25. The absorbent article of claim 18, wherein said absorbent article comprises a sanitary napkin.

* * * * *